US010611088B1

(12) United States Patent
Friedman

(10) Patent No.: US 10,611,088 B1
(45) Date of Patent: Apr. 7, 2020

(54) DEVICE AND METHODS FOR OPTIMIZING POST-CURING TIME OF 3D PRINTED PRODUCTS

(71) Applicant: AdDent, Inc., Danbury, CT (US)

(72) Inventor: Joshua Friedman, Ridgefield, CT (US)

(73) Assignee: AdDent, Inc., Danbury, CT (US)

( * ) Notice: Subject to any disclaimer, the term of this patent is extended or adjusted under 35 U.S.C. 154(b) by 0 days.

(21) Appl. No.: 16/416,987

(22) Filed: May 20, 2019

Related U.S. Application Data

(60) Provisional application No. 62/815,879, filed on Mar. 8, 2019.

(51) Int. Cl.

| | |
|---|---|
| ***B33Y 50/00*** | (2015.01) |
| ***B29C 64/386*** | (2017.01) |
| ***G01N 21/59*** | (2006.01) |
| *G01N 21/17* | (2006.01) |

(52) U.S. Cl.

CPC ............ *B29C 64/386* (2017.08); *B33Y 50/00* (2014.12); *G01N 21/59* (2013.01); *G01N 2021/1761* (2013.01); *G01N 2201/0407* (2013.01)

(58) Field of Classification Search

CPC ... B29C 64/386; B29C 64/379; B29C 64/393; B33Y 50/00; B33Y 10/00; B33Y 50/02; G01N 21/59; B41M 3/008; B41M 5/0011; G05B 2219/35134; G05B 19/4099; G05B 2219/49007; G05B 2219/49023; B41F 23/00; B41J 11/002

USPC ........................................................ 250/221

See application file for complete search history.

(56) References Cited

U.S. PATENT DOCUMENTS

| | | | |
|---|---|---|---|
| 6,485,301 B1 | 11/2002 | Gemunder et al. | |
| 7,175,436 B2 | 2/2007 | Friedman | |
| 2002/0076530 A1 | 6/2002 | MacDougald et al. | |
| 2007/0251403 A1* | 11/2007 | St. John | B41J 11/002 101/424.1 |
| 2007/0259309 A1 | 11/2007 | West et al. | |
| 2008/0120137 A1 | 5/2008 | Nyholm | |
| 2008/0187880 A1 | 8/2008 | Becker et al. | |
| 2019/0091000 A1 | 3/2019 | Kubiak-Essmann et al. | |

* cited by examiner

*Primary Examiner* — Que Tan Le

(74) *Attorney, Agent, or Firm* — Hojka Qadeer, LLC

(57) ABSTRACT

The present disclosure describes a device used to determine the optimal post-curing exposure time for 3D printed products and methods of using the same. The disclosed device is a self-contained multi-chamber radiometer for continuous monitoring of electromagnetic radiation transmitted through 3D printed objects during a post-curing process. The device includes multiple detector ports, including a control port and one or more sample ports. The detector ports may preferably be photocells configured to generate a voltage proportional to the intensity of the incident electromagnetic radiation at specific wavelength(s). The transmittance is directly correlated with the voltage and may be measured using the determined voltages. The disclosed device may further comprise a microprocessor, a memory module for storage of data obtained by the sensors, and one or more communication modules configured to enable wireless communication with a data storage device such as a computer.

20 Claims, 3 Drawing Sheets

DEVICE AND METHODS FOR OPTIMIZING POST-CURING TIME OF 3D PRINTED PRODUCTS

CROSS-REFERENCE TO RELATED APPLICATIONS

This application claims priority to U.S. Provisional Patent Application Ser. No. 62/815,879, filed on Mar. 8, 2019, the disclosure of which is incorporated herein in its entirety by reference.

BACKGROUND

Field of the Invention

The present disclosure relates to determining the optimal post-curing exposure time for 3D printed products.

Description of the Related Art

The development of 3D printing, also known as additive manufacturing, has allowed a variety of products to be readily fabricated. 3D printing has been used to fabricate a diverse array of products in many fields, including engineering models and prototypes, dental products, and jewelry. 3D printing technologies include binder jetting, directed energy deposition, material extrusion, material jetting, powder bed fusion, sheet lamination, and vat photopolymerization.

Vat photopolymerization methods of 3D printing, including stereolithography and digital light processing (DLP), involve the curing of photopolymers by a light source to ultimately generate 3D printed products. Stereolithography and digital light processing rely on the incremental curing of layers that represent the configuration of the product within a sample of a pre-defined vertical thickness. This incremental curing is implemented by using a targeted light source to selectively photo-cure a desired layer of photopolymer resin. By exposing specific photoinitiators to the proper wavelengths of electromagnetic radiation, the resin is photopolymerized to form a semi-solid layer. A plate may be used as a base upon which to build the desired three dimensional object. The object is constructed by sequential layering of printed material with controlled thicknesses, ultimately leading to the formation of the desired product shape. The object is then removed from the vat of polymerizable resin and separated from the build plate upon which its base was established.

Typically, the extent of cure of the initial printed object is quite low—in certain 3D printing applications it may be as low as 20%. In many instances, this results in poor mechanical properties of the 3D printed object. This also results in low biocompatibility for applications that require the latter. An object at this stage of fabrication is referred to as being in a "green state." This partial curing provides an initial shape to the object and ensures covalent bonding between sequential photocured layers. In many 3D printing applications, the object must undergo further treatment after removal from the polymerization vat. In such applications, the object in the green state is rinsed multiple times, typically in an alcohol solution, to remove superficial uncured resin. The object is then placed in a device that emits high intensity, short wavelength radiation (violet to ultraviolet wavelengths) for a pre-determined amount of time. During this process, additional radiant energy penetrates the outer surface of the as-printed object and continues to interact with photoinitiators still unused and present within the depths of the printed object. The overall purpose of this "post-curing" process is to provide higher degrees of resin curing in the interior of the object, which will result in consumption of residual, unreacted internal resin. This further polymerization enhances the mechanical properties of the object. It also significantly improves biocompatibility for applications that require it. During the post-curing process, the density of the object increases.

When performing vat polymerization 3D printing using specific types of commercially available resins (unpolymerized starting materials), the manufacturer of the resin supplies specific instructions to the 3D printer so that the printer emits the proper intensity of light for the proper amount of time when exposing an individual layer, so that the resultant 3D printed object has the desired properties. In many applications, the as-printed object will still require post-curing, as described above. However, there are no sets of specific instructions provided for a post-curing device to adjust the conditions imposed during post-curing. Rather, the resin manufacturer typically merely provides general guidelines for the exposure time or thermal conditions needed for a given maximum thickness of an object undergoing post-curing.

The types and characteristics of devices used for post-curing range widely. Post-curing units may be LED-based and provide narrow wavelength light (405 nm or 385 nm); may incorporate broad-banded fluorescent light sources, such as those commonly used to photo-cure methacrylate-based nail gel formulations; or may use metal halide lights (200-600 W) or xenon-strobing light generators. In addition, some post-curing units also provide chamber heating during the application of post-cure radiation.

Where an end user uses resins from a given manufacturer, and the 3D printer and post-curing device used by the end user were all tested by the resin manufacturer, the end user is typically provided with recommended exposure times to use for objects of varying thicknesses. Data used to derive these recommended exposure times are obtained by the resin manufacturer, in conjunction with the manufacturer of the printer and the manufacturer of the post-curing unit, by flexural strength testing of bar-shaped samples. In that process, as-printed bars are exposed to electromagnetic radiation for different lengths of time in the post-curing device, providing a guide for recommended exposure duration to obtain optimal strength values. However, in many situations an end user uses a post-curing device for which no such strength testing results have been provided. In addition, even when the end user has access to some recommendations, the bar strength value is not always available for the desired thickness of the object being fabricated. Thus, optimal post-cure exposure times for specimens thinner or thicker than that recommended for the as-printed bar are not available. Therefore, end users who are actually fabricating 3D printed products often have little or no idea how long to post-cure a material of a given thickness.

The photoinitiators used to fabricate dental products by vat polymerization 3D printing processes typically absorb electromagnetic radiation with short wavelengths. Thus, in dental applications, the electromagnetic radiation used for curing is typically violet (405 nm) or ultraviolet (385 nm) light. The electromagnetic radiation may be generated using solid state lasers, individual high intensity light emitting diodes (LEDs), or arrays of light emitting diodes (LEDs) that use an electronic masking filter between the light source and target resin to provide the light outline of the layer to be printed.

As discussed above, the properties of 3D printed products are significantly affected by the efficacy of the post-curing process. As there is no standardized protocol for providing an end user with known post-curing conditions to generate 3D printed objects with optimal properties, there thus remains a need for a device that provides an end user with real-time recommendations for the optimal post-curing exposure.

SUMMARY

The present disclosure describes a device used to determine the optimal post-curing exposure time for 3D printed products and methods of using the same. The disclosed device is a self-contained multi-chamber radiometer for continuous monitoring of electromagnetic radiation transmitted through 3D printed objects during a post-curing process.

The device comprises two or more detector ports, wherein each detector port comprises a sensor. At least one detector port is a control port, where the control port sensor is configured to measure the transmittance at a specific wavelength or within a specified range of wavelengths where no 3D printed object is placed on the control port. At least one other detector port is a sample port, where the sample port sensor is configured to measure the transmittance at a specific wavelength or within a specified range of wavelengths through a 3D printed object placed on the sample port. The device may preferably comprise two or more sample ports.

The sensors may preferably be photocells. In some embodiments, each sensor may be configured to generate upon irradiation a voltage proportional to the intensity of the incident electromagnetic radiation at a specific wavelength or within a specified range of wavelengths. Thus the transmittance at the specific wavelength or within the specified range of wavelengths may be directly correlated with the voltage generated.

The one or more sample port sensors may be situated at specified depths within the device relative to the control port sensor such that the one or more sample port sensors are each configured to receive a sample of a specified thickness.

The disclosed device may preferably be configured to be housed within a post-curing device.

In some embodiments, the disclosed device may further comprise a microprocessor and a memory module, where the microprocessor is configured to record data obtained by the sensors for storage on the memory module.

In some embodiments, the disclosed device may further comprise one or more communication modules, hereinafter termed radiometer communication modules, that are configured to enable wireless communication with a data storage device.

Methods of optimizing the post-curing time for a 3D printed object are disclosed herein. The methods comprise use of the disclosed device to determine the optimum post-curing time for a 3D printed object. In some embodiments, each sensor is a photocell configured to generate upon irradiation a voltage proportional to the intensity of the incident electromagnetic radiation at a specific wavelength or within a specified range of wavelengths. In such embodiments, the transmittance at the specific wavelength or within the specified range of wavelengths is directly correlated with the voltage generated. In such embodiments, the method may comprise the following steps:

(1) a first voltage may be measured at the control port;

(2) a test sample of the 3D printed object with a specified thickness may be placed on a sample port and a second voltage may be measured at the sample port; and (3) the ratio of the second voltage to the first voltage may be determined.

When a radiometer with multiple sample ports is used, a test sample of the 3D printed object may be placed on each sample port and steps (2)-(3) may be repeated for each test sample. In such embodiments, the test samples may preferably be of varying thicknesses.

DETAILED DESCRIPTION OF THE ILLUSTRATED EMBODIMENTS

Figure 1:
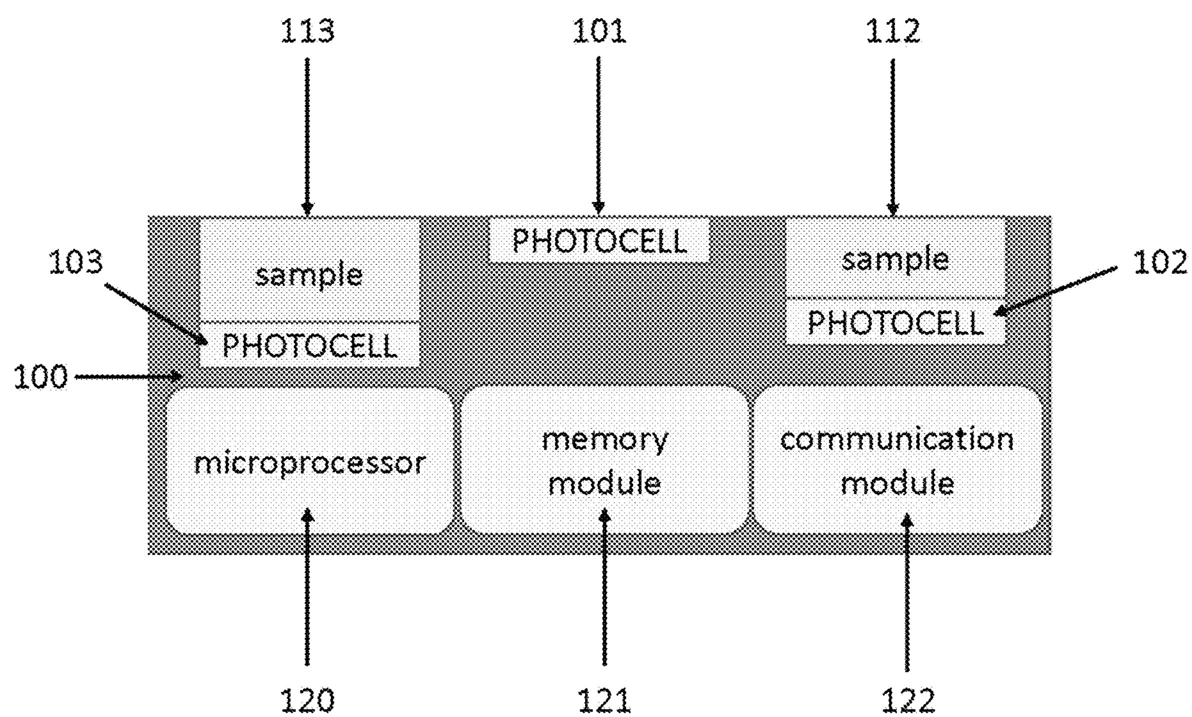
FIG. 1 shows a cross-sectional block diagram of an embodiment of the disclosed device.

The present disclosure describes a device used to determine the optimal post-curing exposure time for 3D printed products and methods of using the same. The disclosed device is a self-contained multi-chamber radiometer for continuous monitoring of electromagnetic radiation transmitted through 3D printed objects during a post-curing process.

3D Printing and Post-Curing of Dental Products

Restorative dental devices, such as dentures, surgical guides, temporary restorations, and bite splints, and ancillary dental products, such as models, may be fabricated using 3D printing processes. Such devices and products may be fabricated in dental laboratories, or dental offices may alternatively fabricate such devices and products in-house. Commercial dental 3D printing employs a number of proprietary, photo-curable resins that are each specifically formulated for use in fabricating a specific type of end product.

Post-curing devices used in post-curing of 3D printed objects for dental applications typically irradiate 3D printed objects placed therein at wavelengths between 350 nm and 470 nm.

The photoinitiators used to fabricate dental products by vat polymerization 3D printing processes generally absorb light in the unreacted state and photobleach upon exposure to light to form free radicals that are necessary to initiate the polymerization process. Photobleaching is the photochemical alteration of a molecule (photolysis) such that it is permanently unable to absorb light of a specific wavelength. Thus, the reacted photoinitiators no longer absorb light at the specific wavelength after their initial exposure to light, while unreacted photoinitiators continue to absorb light. It is therefore possible to monitor the extent of polymerization in the interior of an as-printed item during a post-curing process by measuring the change in light absorption characteristics imparted by further reaction of residual unreacted photoinitiators, as the unreacted photoinitiators will photobleach upon photochemical reacting. As a result of consumption of additional photoinitiator during post-curing, the 3D printed object will transmit more light of the wavelength(s) used for post-curing. Thus, when the change in light transmission reaches a plateau, further exposure of the object to post-curing electromagnetic radiation is no longer necessary. This phenomenon is applicable to the wide range of photoinitiators used throughout UV-induced 3D printing processes.

Although ultraviolet light is known to interact directly with unsaturated C=C of acrylate and methacrylate moieties, the relevant wavelengths are significantly lower (around 250 nm) than the wavelengths used in dental post-curing units. Thus, exposure of as-printed dental objects during the post-curing process only activates unused photoinitiator positioned in the interior of the object and does not cause direct reaction with the unpolymerized C=C of acrylates and methacrylates.

Device for Monitoring Post-Curing Light Transmission

The disclosed device is a self-contained multi-chamber radiometer for continuous monitoring of electromagnetic radiation transmitted through 3D printed objects during a post-curing process.

The device comprises two or more detector ports, wherein each detector port comprises a sensor. At least one detector port is a control port, where the control port sensor is configured to measure the transmittance at a specific wavelength or within a specified range of wavelengths where no 3D printed object is placed on the control port. At least one other detector port is a sample port, where the sample port sensor is configured to measure the transmittance at a specific wavelength, or within a specified range of wavelengths, through a 3D printed object placed on the sample port. The device may preferably comprise two or more sample ports.

The sensors may preferably be photocells. In some embodiments, each sensor may be configured to generate upon irradiation a voltage proportional to the intensity of the incident electromagnetic radiation at a specific wavelength or within a specified range of wavelengths. Thus the transmittance at the specific wavelength, or within the specified range of wavelengths, may be directly correlated with the voltage generated.

The one or more sample port sensors may be situated at specified depths within the device relative to the control port sensor such that the one or more sample port sensors are each configured to receive a sample of a specified thickness.

The disclosed device may preferably be configured to be housed within a post-curing device.

In some embodiments, the disclosed device may be battery operated. In other embodiments, the disclosed device may be operated by an internal or external power supply.

In some embodiments, the disclosed device may further comprise a microprocessor and a memory module, where the microprocessor is configured to record data obtained by the sensors for storage on the memory module.

In some embodiments, the disclosed device may further comprise one or more communication modules, hereinafter termed radiometer communication modules, that are configured to enable wireless communication with a data storage device. The data storage device may also comprise one or more communication modules. The one or more radiometer communication modules may comprise one or more Bluetooth, Wi-Fi, ZigBee, or other radio frequency-based modules. In alternative embodiments, the one or more radiometer communication modules may comprise one or more infrared or other optically-based modules. The one or more data storage device communication modules may comprise one or more Bluetooth, Wi-Fi, ZigBee, or other radio frequency-based modules. In alternative embodiments, the one or more data storage device communication modules may comprise one or more infrared or other optically-based modules. In some embodiments, additional communication modules may also act to relay signals between other communication modules, such as to extend the range of communication, or to convert transmissions between different formats, such as Wi-Fi to Bluetooth or ZigBee to infrared.

The data stored by the memory module may be wirelessly transmitted to a data storage device using the one or more communication modules.

Wireless transmission of data using the disclosed communication modules may also be used to allow a computer to update and adapt the disclosed device to improve its performance. For example, a firmware upgrade may be pushed out by a computer. As another example, a computer may send instructions to a post-curing device restricting operation of the post-curing device to prevent a user from damaging a selected 3D printed object.

Wireless transmission of data using the disclosed communication modules may also be used to allow monitoring or controlling of the radiometric output using a handheld computer, such as a smartphone or tablet.

Methods of Optimizing Post-Curing Time

Methods of optimizing the post-curing time for a 3D printed object are disclosed herein. The methods comprise use of the disclosed device to determine the optimum post-curing time for a 3D printed object.

In some embodiments, each sensor is a photocell configured to generate upon irradiation a voltage proportional to the intensity of the incident electromagnetic radiation at a specific wavelength or within a specified range of wavelengths. In such embodiments, the transmittance at the specific wavelength or within the specified range of wavelengths is directly correlated with the voltage generated. In such embodiments, the method may comprise the following steps:

(1) a first voltage may be measured at the control port;

(2) a test sample of the 3D printed object with a specified thickness may be placed on a sample port and a second voltage may be measured at the sample port; and (3) the ratio of the second voltage to the first voltage may be determined.

When a radiometer with multiple sample ports is used, a test sample of the 3D printed object may be placed on each sample port and steps (2)-(3) may be repeated for each test sample. In such embodiments, the test samples may preferably be of varying thicknesses. The samples to be placed in the ports are made using the same 3D printing resin from which the anticipated 3D printed object will be generated. Freshly 3D printed specimens of dimensions made to fit the radiometer ports will be rinsed in the manner that the anticipated future 3D printed objects will be treated, will be dried using standard methods of drying 3D printed objects after rinsing, and will be immediately placed into the appropriate ports of the radiometer for the specimen thicknesses that will be monitored during the post-curing process.

Because light sensor voltage is directly correlated with light transmittance, an increase in the voltage generated over time at the sample port will reflect an increase in transmittance. Because the photoinitiator will photobleach upon curing, an increase in transmittance corresponds to more reacted photoinitiator within the test sample. When the transmittance reaches a plateau and no longer increases an appreciable amount over time, this indicates that no additional photoinitiator is reacting and the optimum duration for post-curing has been achieved.

In some embodiments, the test sample is rinsed prior to its introduction into the post-curing device. The rinse may preferably be with an alcohol solvent. In other embodiments, the test sample is not rinsed prior to its introduction into the post-curing device.

In some embodiments, the test samples are 3D printed discs of varying thicknesses.

In some embodiments, the photocells may be configured to generate upon irradiation with electromagnetic radiation of wavelength between 350 nm and 400 nm a voltage proportional to the intensity of the incident (and transmitted) electromagnetic radiation. In some embodiments, the photocells may be configured to generate upon irradiation with electromagnetic radiation of wavelength between 350 nm and 450 nm a voltage proportional to the intensity of the incident (and transmitted) electromagnetic radiation. In some embodiments, the photocells may be configured to generate upon irradiation with electromagnetic radiation between 300 nm and 800 nm a voltage proportional to the intensity of the incident (and transmitted) electromagnetic radiation. In some embodiments, the photocells may be configured to generate upon irradiation with electromagnetic radiation of a specified range of wavelengths between 300 nm and 800 nm a voltage proportional to the intensity of the incident (and transmitted) electromagnetic radiation.

The use of a control port in the disclosed methods allows a user to account for the effect of variance in the intensity of electromagnetic radiation generated by the post-curing device over time. If no control port is used, the user will not be able to eliminate variance in the intensity of electromagnetic radiation generated by the post-curing device over time as a possible reason for a change in voltage.

By simultaneously exposing unrinsed and rinsed 3D printed discs of varying thicknesses to the post-curing process, a user may establish an optimal duration for post-curing for a 3D printed object fabricated from a specific resin. This optimal duration may vary between batches of the same resin, and thus the disclosed methods allow a user to fine tune post-curing for a 3D printed object fabricated from a specific batch of a given resin. The disclosed device will allow a user to create a calibration routine to set the optimal post-curing time for each new batch of resin used for 3D printing for a 3D printed object of a given thickness.

In some embodiments, the minimum amount of time for optimal post-curing of a specified 3D printed object may be wirelessly transmitted from the device to a data storage device. In some embodiments, the microprocessor may be configured to send a signal to the post-curing device to automatically turn off when the optimal post-curing time has been reached. In other embodiments, a visual or audio signal, such as a flickering LED or a musical chime, may be used to indicate when the optimal curing time has been reached.

DETAILED DESCRIPTION OF THE DRAWINGS

FIG. 1 shows a cross-sectional block diagram of an embodiment 100 of the disclosed device, including control port sensor 101, sample port sensor 102, sample port sensor 103, test sample 112, test sample 113, microcontroller 120, memory module 121, and communication module 122. Sample port sensor 102 and sample port sensor 103 may be situated at appropriate depth offsets from control port sensor 101 within device 100 to receive test samples 112 and 113 respectively. Test sample 113 has a thickness that is greater than the thickness of test sample 112. For example, test sample 113 may be 3 mm thick and test sample 112 may be 2 mm thick. Voltage data obtained by control port sensor 101, sample port sensor 102, and sample port sensor 103 may be recorded using microprocessor 120 and may be stored in memory module 121. The voltage data may then be wirelessly transmitted to an external data storage device (not shown) using communication module 122. Communication module 122 may be, for example, a Bluetooth module.

Figure 2:
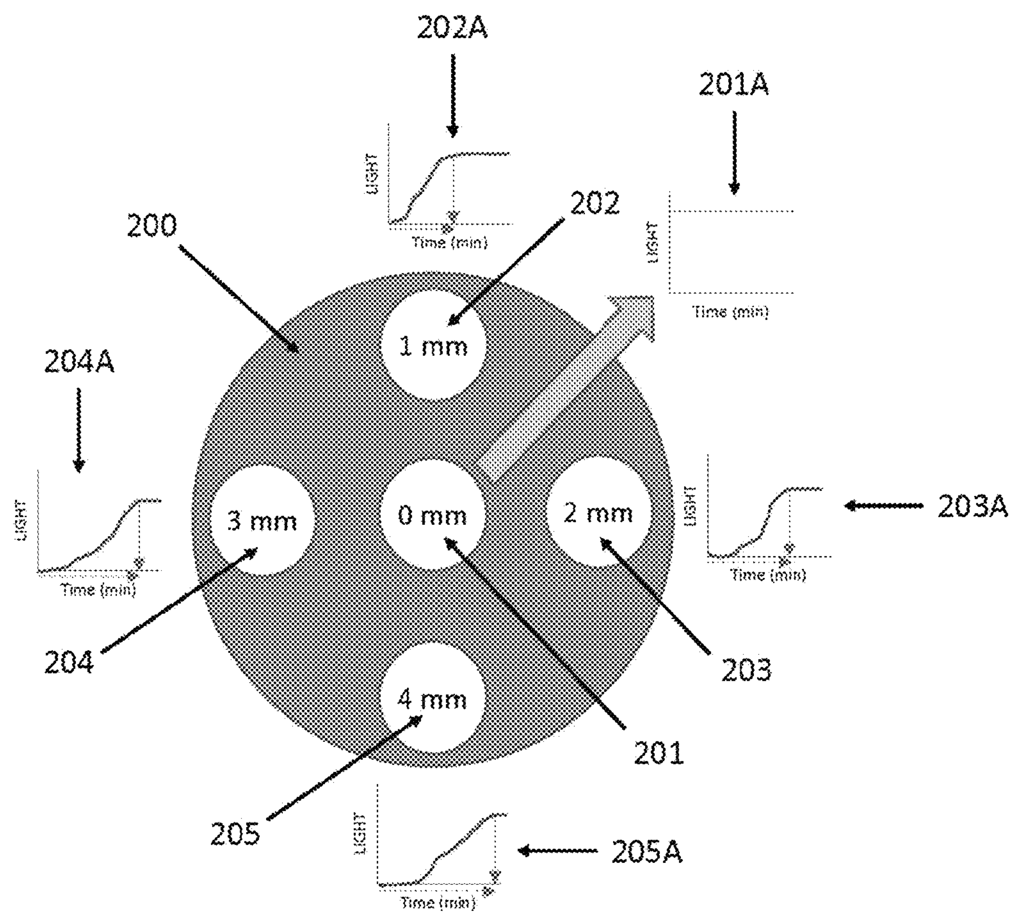
FIG. 2 shows a top view block diagram of an embodiment of the disclosed device.

FIG. 2 shows a top view block diagram of an embodiment 200 of the disclosed device, including control port sensor 201, sample port sensor 202 configured to receive a sample with a 1 mm thickness, sample port sensor 203 configured to receive a sample with a 2 mm thickness, sample port sensor 204 configured to receive a sample with a 3 mm thickness, and sample port sensor 205 configured to receive a sample with a 4 mm thickness. Graphical depictions 201A, 202A, 203A, 204A, and 205A illustrate results for transmittance of electromagnetic radiation obtained from voltage data for sensors 201, 202, 203, 204, and 205 respectively as a function of post-curing time. The graphical depictions show differing plateau times for different sample thicknesses, displayed as vertical arrowed lines that indicate a maximum in transmittance for a specified object thickness and dashed horizontal lines that indicate the post-curing exposure duration needed to reach this plateau value. Upon reaching the plateau value, further exposure to post-curing electromagnetic radiation will not result in additional curing to an appreciable extent.

Figure 3:
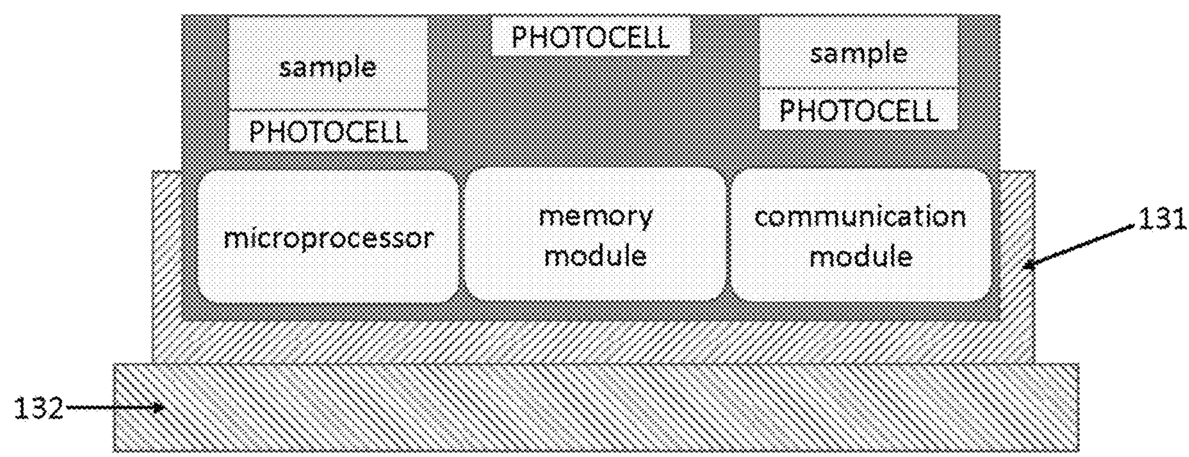
FIG. 3 shows a cross-sectional block diagram of an embodiment of the disclosed device shown in FIG. 1 seated in a rotational homogenizer.

FIG. 3 shows a cross-sectional block diagram of an embodiment of the disclosed device shown in FIG. 1 seated in a rotational homogenizer. The rotational homogenizer obviates any concerns regarding nonhomogeneous distribution of electromagnetic radiation within the post-curing device. The radiometer is placed into a rotating platform 131 which is form-fitted into the base 132 of the post-curing device. A motor (not shown) may be used to rotate platform 131 such that the various sensors of the radiometer are homogeneously exposed to electromagnetic radiation emitted by the post-curing device. In some embodiments, the rotation may preferably be between 1 rpm and 4 rpm.

The previous description of the disclosed embodiments is provided to enable any person skilled in the art to make or use the invention disclosed herein. Various modifications to these embodiments will be readily apparent to those skilled in the art, and the generic principles defined herein may be applied to other embodiments without departing from the spirit or scope of the disclosure. The examples are intended to be merely illustrative and are not intended to limit or otherwise restrict the invention. Thus, the present disclosure is not intended to be limited to the embodiments shown herein but is to be accorded the widest scope consistent with the principles and novel features disclosed herein.

All references cited herein are expressly incorporated by reference.

What is claimed is:

1. A device suitable for determining the optimal post-curing time for a 3D printed object, wherein the device comprises a radiometer comprising:

a control port comprising a control port sensor; and one or more sample ports, wherein each sample port comprises a sample port sensor;

wherein the device is configured to determine the optimal post-curing time for a 3D printed object by performing the following steps:

a. placing a test sample of the 3D printed object with a first thickness on a first sample port;

b. irradiating the test sample and the control port from a start time until at least an end time;

c. performing the following iterative steps (i)-(iii) at a first time:

i. measuring a control voltage at the control port;

ii. measuring a sample voltage at the first sample port; and iii. determining a ratio of the sample voltage to the control voltage;

d. iteratively repeating steps (i)-(iii) until the end time at an iteration time that is after the first time, wherein the end time is the time when the ratio is approximately the same for at least two successive iterative repetitions of steps (i)-(iii);

e. identifying a cure time as the time at which the ratio is first approximately the same as the ratio at the end time; and f. determining the difference between the cure time and the start time to determine the optimal post-curing time.

2. The device of claim 1 further comprising a microprocessor, a memory module, and one or more communication modules.

3. The device of claim 1 comprising at least two sample ports.

4. The device of claim 2 comprising at least two sample ports.

5. The device of claim 3, wherein the control port sensor and sample port sensors are photocells.

6. The device of claim 4, wherein the control port sensor and sample port sensors are photocells.

7. The device of claim 5, wherein each photocell is configured to generate upon irradiation a voltage proportional to the intensity of the incident electromagnetic radiation at a specific wavelength or within a specified range of wavelengths.

8. The device of claim 6, wherein each photocell is configured to generate upon irradiation a voltage proportional to the intensity of the incident electromagnetic radiation at a specific wavelength or within a specified range of wavelengths.

9. The device of claim 8, wherein a first sample port sensor is situated at a first depth within the device relative to the control port sensor and a second sample port sensor is situated at a second depth within the device relative to the control port sensor, wherein the first depth is different from the second depth.

10. The device of claim 8, wherein the device is configured to be housed within a post-curing device.

11. The device of claim 2, wherein the microprocessor is configured to record data obtained by the sensors for storage on the memory module.

12. The device of claim 8, wherein the microprocessor is configured to record data obtained by the sensors for storage on the memory module.

13. The device of claim 11, wherein the one or more communication modules are configured to enable wireless communication with a data storage device.

14. The device of claim 12, wherein the one or more communication modules are configured to enable wireless communication with a data storage device.

15. The device of claim 13, wherein the microcontroller is configured to be controlled using a handheld computer.

16. The device of claim 14, wherein the microcontroller is configured to be controlled using a handheld computer.

17. The device of claim 10 further comprising a rotational homogenizer.

18. A method of determining the optimal post-curing time for a 3D printed object using the device of claim 1, the method comprising:

a. placing a test sample of the 3D printed object with a first thickness on a first sample port;

b. irradiating the test sample and the control port from a start time until at least an end time;

c. performing the following iterative steps (i)-(iii) at a first time:

i. measuring a control voltage at the control port;

ii. measuring a sample voltage at the first sample port; and iii. determining a ratio of the sample voltage to the control voltage;

d. iteratively repeating steps (i)-(iii) until the end time at an iteration time that is after the first time, wherein the end time is the time when the ratio is approximately the same for at least two successive iterative repetitions of steps (i)-(iii);

e. identifying a cure time as the time at which the ratio is first approximately the same as the ratio at the end time; and f. determining the difference between the cure time and the start time to determine the optimal post-curing time.

19. A method of determining the optimal post-curing time for a 3D printed object using the device of claim 3, the method comprising:

a. placing a first test sample of the 3D printed object with a first thickness on a first sample port;

b. placing a second test sample of the 3D printed object with a second thickness on a second sample port;

c. irradiating the first test sample, the second test sample, and the control port from a start time until at least an end time;

d. performing the following iterative steps (i)-(v) at a first time:

i. measuring a control voltage at the control port;

ii. measuring a first sample voltage at the first sample port;

iii. measuring a second sample voltage at the second sample port;

iv. determining a first ratio of the first sample voltage to the control voltage; and v. determining a second ratio of the second sample voltage to the control voltage;

e. iteratively repeating steps (i)-(v) until the end time at an iteration time that is after the first time, wherein the end time is the time when the first ratio is approximately the same for at least two successive iterative repetitions of steps (i)-(v) and the second ratio is approximately the same for at least two successive iterative repetitions of steps (i)-(v);

f. identifying a first cure time as the time at which the first ratio is first approximately the same as the ratio at the end time;

g. identifying a second cure time as the time at which the second ratio is first approximately the same as the ratio at the end time;

h. determining the difference between the first cure time and the start time to determine the optimal post-curing time for the first test sample; and i. determining the difference between the second cure time and the start time to determine the optimal post-curing time for the second test sample.

20. The method of claim 19, wherein the control port sensor and each sample port sensor is a photocell configured to generate upon irradiation a voltage proportional to the intensity of the incident electromagnetic radiation at a specific wavelength or within a specified range of wavelengths, wherein the first thickness is different from the second thickness, and wherein the first sample port sensor is situated at a first depth within the device relative to the control port sensor and the second sample port sensor is situated at a second depth within the device relative to the control port sensor, wherein the first depth is different from the second depth.

* * * * *